(12) United States Patent
Clark et al.

(10) Patent No.: US 7,652,116 B2
(45) Date of Patent: *Jan. 26, 2010

(54) FLUOROCHEMICAL URETHANE-SILANE COMPOUNDS AND AQUEOUS COMPOSITIONS THEREOF

(75) Inventors: Gregory D. Clark, St. Paul, MN (US); Patrick J. Hager, Woodbury, MN (US); Jay S. Schlechte, Oakdale, MN (US); John C. Clark, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 33 days.

This patent is subject to a terminal disclaimer.

(21) Appl. No.: 11/765,914

(22) Filed: Jun. 20, 2007

(65) Prior Publication Data

US 2008/0314287 A1    Dec. 25, 2008

(51) Int. Cl.
*C08G 77/04* (2006.01)
(52) U.S. Cl. ..................................... 528/28
(58) Field of Classification Search ............... 528/28, 528/61, 55, 70, 71; 524/588, 589, 591
See application file for complete search history.

(56) References Cited

U.S. PATENT DOCUMENTS

| | | |
|---|---|---|
| 3,493,424 A | 2/1970 | Mohrlok et al. |
| 4,351,736 A | 9/1982 | Steinberger et al. |
| 4,378,250 A | 3/1983 | Treadway et al. |
| 4,508,916 A | 4/1985 | Newell et al. |
| 4,781,844 A | 11/1988 | Kortmann et al. |
| 5,073,442 A | 12/1991 | Knowlton et al. |
| 5,274,159 A | 12/1993 | Pellerite et al. |
| 5,679,754 A * | 10/1997 | Larson et al. .................. 528/28 |
| 6,803,109 B2 | 10/2004 | Qiu et al. |
| 7,094,829 B2 | 8/2006 | Audenaert et al. |
| 2005/0075471 A1 | 4/2005 | Fan et al. |
| 2005/0171279 A1 | 8/2005 | Coté et al. |
| 2006/0029799 A1 | 2/2006 | Sebastian et al. |

FOREIGN PATENT DOCUMENTS

| | | |
|---|---|---|
| DE | 100 08 150 A 1 | 8/2001 |
| WO | WO 01/44209 A1 | 6/2001 |
| WO | WO 2006/102383 A1 | 9/2006 |
| WO | WO 2008/073689 A1 | 6/2008 |

OTHER PUBLICATIONS

Dietliker, "Photoinitiators for Free Radical and Cationic Polymerisation", Chemistry & Technology of UV & EB Formulation for Coatings, Inks & Paints, (1991), pp. 276-298, vol. III, SITA Technology Ltd., London, England.
U.S. Appl. No. 11/765,938, filed Jun. 20, 2007, entitled "Fluorochemical Urethane Compounds and Aqueous Compositions Thereof".

* cited by examiner

*Primary Examiner*—Daniel M Sullivan
*Assistant Examiner*—Chukwuma O Nwaonicha
(74) *Attorney, Agent, or Firm*—Kent S. Kokks

(57) ABSTRACT

Fluorochemical urethane compounds and coating compositions derived therefrom are described. The compounds and composition may be used in treating substrates, in particular substrates having a hard surfaces such as ceramics or glass, to render them hydrophilic, oleophobic and easy to clean.

20 Claims, No Drawings

FLUOROCHEMICAL URETHANE-SILANE COMPOUNDS AND AQUEOUS COMPOSITIONS THEREOF

FIELD OF THE INVENTION

The present invention relates to fluorochemical urethane compounds and coating compositions derived therefrom, which may be used in treating substrates, in particular substrates having a hard surface such as ceramics or glass, to render them hydrophilic, oil, stain, and dirt repellent.

BACKGROUND

Although many fluorinated compositions are known in the art for treating substrates to render them oil and water repellent, there continues to be a desire to provide further improved compositions for the treatment of substrates, in particular substrates having a hard surface such as ceramics, glass and stone, in order to render them water-repellent (hydrophobic), oil-repellent (oleophobic), and easy to clean. There is also a need for treating, in order to render hydrophilic, oleophobic, and easy to clean.

Desirably, such compositions and methods employing them can yield coatings that have improved properties. In particular, it would be desirable to improve the durability of the coating, including an improved abrasion resistance of the coating. Furthermore, improving the ease of cleaning of such substrates while using less detergents, water or manual labor, is not only a desire by the end consumer, but has also a positive impact on the environment. The compositions may be applied in an easy and safe way and are compatible with existing manufacturing methods. Preferably, the compositions will fit easily into the manufacturing processes that are practiced to produce the substrates to be treated.

SUMMARY

The present invention provides fluorochemical urethane compounds of the formula

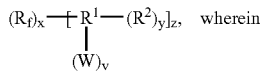

$R_f$ is a fluorine-containing group, $R^1$ is the residue of a polyisocyanate,

W is

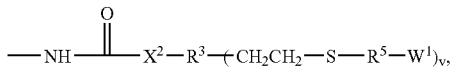

where $W^1$ is a water-solubilizing group, and v is 1 or 2;

$R^2$ is of the formula:

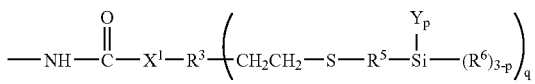

wherein $X^1$ is —O— or —NR$^4$—, where $R^4$ is H or $C_1$-$C_4$ alkyl, $R^3$ is a polyvalent alkylene or arylene groups, or combinations thereof, said alkylene groups optionally containing one or more catenary oxygen atoms;

$R^5$ is a divalent alkylene group, said alkylene groups optionally containing one or more catenary oxygen atoms;

Y is a hydrolysable group, $R^6$ is a monovalent alkyl or aryl group, p is 1, 2 or 3, and q is 1 to 5, x and y are each independently at least 1, and z is independently 1 or 2.

These compounds or oligomers may comprise the free-radical addition reaction product of an thiosilane with a fluorine-containing urethane compound having pendent ethylenically unsaturated group groups, said urethane compound comprising the reaction product of a polyisocyanate, a nucleophilic fluorinated compound having one or two nucleophilic, isocyanate-reactive functional groups, and at least one nucleophilic ethylenically unsaturated compound. In another embodiment, the compounds may comprise the free-radical addition reaction product of a thiosilane and a water-solubilizing compound with a nucleophilic, ethylenically unsaturated compound, and subsequent reaction product with the polyisocyanate, and the fluorine-containing nucleophilic compound.

Unless otherwise stated, the following terms used in the specification and claims have the meanings given below:

"Alkyl" means a linear or branched, cyclic or acylic, saturated monovalent hydrocarbon radical having from one to about twelve carbon atoms, e.g., methyl, ethyl, 1-propyl, 2-propyl, pentyl, and the like.

"Alkylene" means a linear saturated divalent hydrocarbon radical having from one to about twelve carbon atoms or a branched saturated divalent hydrocarbon radical having from three to about twelve carbon atoms, e.g., methylene, ethylene, propylene, 2-methylpropylene, pentylene, hexylene, and the like.

"Alkoxy" means an alkyl having a terminal oxygen atom, e.g. $CH_3$—O—, $C_2H_5$—O—, and the like.

"Aralkylene" means an alkylene radical defined above with an aromatic group attached to the alkylene radical, e.g., benzyl, pyridylmethyl, 1-naphthylethyl, and the like. "Cured chemical composition" means that the chemical composition is dried or solvent has evaporated from the chemical composition from ambient temperature or higher until dryness, up to approximately 24 hours. The composition may further be crosslinked as result of siloxane bonds formed between the urethane compounds.

"Fluorinated nucleophilic compound" means a compound having one or two nucleophilic, isocyanate-reactive functional groups, such as a hydroxyl group or an amine group, and a perfluoroalkyl, perfluoroalkylene, perfluorooxyalkyl or perfluorooxyalkylene group, e.g. $CF_9SO_2N(CH_3)CH_2CH_2OH$, $C_4F_9CH_2CH_2OH$, $C_2F_5O(C_2F_4O)_3CF_2CONHC_2H_4OH$, c-$C_6F_{11}CH_2OH$, $HOCH_2CH_2C_4F_8CH_2CH_2OH$, and the like.

"Fluorochemical urethane compounds" refers to compounds of Formula I, and will include those having urethane linkages per se, or alternatively urea and/or thiourea linkages.

"Hard substrate" means any rigid material that maintains its shape, e.g., glass, ceramic, concrete, natural stone, wood, metals, plastics, and the like.

"Oxyalkoxy" has essentially the meaning given above for alkoxy except that one or more oxygen atoms may be present in the alkyl chain and the total number of carbon atoms present may be up to 50, e.g. CH$_3$CH$_2$OOCH$_2$CH$_2$O—, C$_4$H$_9$OCH$_2$CH$_2$OCH$_2$CH$_2$O—, CH$_3$O(CH$_2$CH$_2$O)$_n$H, and the like.

"Oxyalkyl" has essentially the meaning given above for alkyl except that one or more oxygen heteroatoms may be present in the alkyl chain, these heteroatoms being separated from each other by at least one carbon, e.g., CH$_3$CH$_2$OCH$_2$CH$_2$—, CH$_3$CH$_2$OCH$_2$CH$_2$OCH(CH$_3$)CH$_2$—, C$_4$F$_9$CH$_2$OCH$_2$CH$_2$—, and the like.

"Oxyalkylene" has essentially the meaning given above for alkylene except that one or more oxygen heteroatoms may be present in the alkylene chain, these heteroatoms being separated from each other by at least one carbon, e.g., —CH$_2$OCH$_2$O—, —CH$_2$CH$_2$OCH$_2$CH$_2$—, —CH$_2$CH$_2$OCH$_2$CH$_2$CH$_2$—, and the like.

"Halo" means fluoro, chloro, bromo, or iodo, preferably fluoro and chloro.

"Perfluoroalkyl" has essentially the meaning given above for "alkyl" except that all or essentially all of the hydrogen atoms of the alkyl radical are replaced by fluorine atoms and the number of carbon atoms is from 1 to about 12, e.g. perfluoropropyl, perfluorobutyl, perfluorooctyl, and the like.

"Perfluoroalkylene" has essentially the meaning given above for "alkylene" except that all or essentially all of the hydrogen atoms of the alkylene radical are replaced by fluorine atoms, e.g., perfluoropropylene, perfluorobutylene, perfluorooctylene, and the like "Perfluorooxyalkyl" has essentially the meaning given above for "oxyalkyl" except that all or essentially all of the hydrogen atoms of the oxyalkyl radical are replaced by fluorine atoms and the number of carbon atoms is from 3 to about 100, e.g. CF$_3$CF$_2$OCF$_2$CF$_2$—, CF$_3$CF$_2$O(CF$_2$CF$_2$O)$_3$CF$_2$CF$_2$—, C$_3$F$_7$O(CF(CF$_3$)CF$_2$O)$_s$CF(CF$_3$)CF$_2$—, where s is (for example) from about 1 to about 50, and the like.

"Perfluorooxyalkylene" has essentially the meaning given above for "oxyalkylene" except that all or essentially all of the hydrogen atoms of the oxyalkylene radical are replaced by fluorine atoms, and the number of carbon atoms is from 3 to about 100, e.g., —CF$_2$OCF$_2$—, or —[CF$_2$—CF$_2$—O]$_r$—[CF(CF$_3$)—CF$_2$—O]$_s$—; wherein r and s are (for example) integers of 1 to 50.

"Perfluorinated group" means an organic group wherein all or essentially all of the carbon bonded hydrogen atoms are replaced with fluorine atoms, e.g. perfluoroalkyl, perfluorooxyalkyl, and the like.

"Polyfunctional isocyanate compound" or "polyisocyanate" means a compound containing an average of greater than one, preferably two or more isocyanate groups, —NCO, attached to a multivalent organic group, e.g. hexamethylene diisocyanate, the biuret and isocyanurate of hexamethylene diisocyanate, and the like.

"Nucleophilic ethylenically unsaturated compound" means an organic compound with at least one isocyanate-reactive group per molecule, and at least one ethylenically unsaturated group, including vinyl, allyl and allyloxy groups.

"Water-solubilizing compound" means an organic compound with at least one thiol group per molecule, and at least one water-solubilizing group.

DETAILED DESCRIPTION

The present invention provides novel fluorochemical urethane compounds of the formula:

wherein $R_f$ is a fluorine-containing group, comprising a monovalent perfluoroalkyl or a perfluorooxyalkyl group, or a divalent perfluoroalkylene or a perfluorooxyalkylene group, $R^1$ is the residue of a polyisocyanate, where $W^1$ is a water-solubilizing group-containing moiety, and v is 1 or 2;

$R^2$ is of the formula:

wherein $X^1$ is —O— or —NR$^4$—, where $R^4$ is H or $C_1$-$C_4$ alkyl, and v is 1 or 2;

$R^2$ is of the formula:

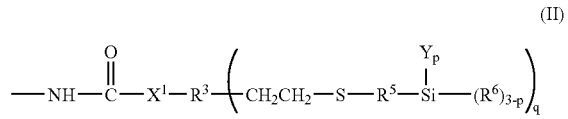

wherein $X^1$ is —O— or —NR$^4$—, where $R^4$ is H or $C_1$-$C_4$ alkyl, $R^3$ is a polyvalent alkylene or arylene groups, or combinations thereof, said alkylene groups optionally containing one or more catenary oxygen atoms;

$R^5$ is a divalent alkylene group, said alkylene groups optionally containing one or more catenary oxygen atoms;

Y is a hydrolysable group, $R^6$ is a monovalent alkyl or aryl group, p is 1, 2 or 3, preferably 3, and q is 1 to 5, preferably 2 to 5, Although the inventors do not wish to be bound by theory, compounds of the above formula I are believed to undergo a condensation reaction with the substrate surface to form a siloxane layer via hydrolysis or displacement of the hydrolysable "Y" groups of Formula II. In this context, "siloxane" refers to —Si—O—Si— bonds to which are attached to compounds of Formula I. In the presence of water, the "Y" groups will undergo hydrolysis "Si—OH" groups, and further condensation to siloxanes.

A coating prepared from the coating composition that includes compounds of Formula I includes the perfluoropolyether silanes per se, as well as siloxane derivatives resulting from bonding to the surface of a preselected substrate. The coatings can also include unreacted or uncondensed "Si—Y" groups and unreacted or hydrolyzed isocyanate groups. The composition may further contain may also contain additional materials such as oligomeric perfluoropolyether monohydrides, starting materials and perfluoropolyether alcohols and esters, and silsesquioxanes. Likewise, coated fluorochemical urethanes may include the silanes of Formula I per se, as well as the siloxane derivatives resulting from reaction with the substrate surface.

In one embodiment, the invention provides a coating composition comprising an aqueous solution, dispersion or suspension compound of Formula I. Alternatively, the invention provides a coating composition comprising an organic solvent solution of the compounds of Formula I. Further, the present invention provides a method of coating comprising the steps of providing contacting a substrate with a coating composition comprising the compound of Formula I and a solvent or water. The coating composition may further comprise an acid. In one embodiment the method comprises contacting a substrate with a coating composition comprising the silane of Formula I, and subsequently contacting the substrate with an aqueous acid.

Polyisocyanate compounds useful in preparing the fluorochemical compounds of Formula I comprise isocyanate groups attached to the multivalent organic group that can comprise a multivalent aliphatic, alicyclic, or aromatic moiety ($R^1$); or a multivalent aliphatic, alicyclic or aromatic moiety attached to a biuret, an isocyanurate, or a uretdione, or mixtures thereof. Preferred polyfunctional isocyanate compounds contain at least two isocyanate (—NCO) radicals. Compounds containing at least two —NCO radicals are preferably comprised of di- or trivalent aliphatic, alicyclic, aralkyl, or aromatic groups to which the —NCO radicals are attached. Aliphatic di- or trivalent groups are preferred.

Representative examples of suitable polyisocyanate compounds include isocyanate functional derivatives of the polyisocyanate compounds as defined herein. Examples of derivatives include, but are not limited to, those selected from the group consisting of ureas, biurets, allophanates, dimers and trimers (such as uretdiones and isocyanurates) of isocyanate compounds, and mixtures thereof. Any suitable organic polyisocyanate, such as an aliphatic, alicyclic, aralkyl, or aromatic polyisocyanate, may be used either singly or in mixtures of two or more.

The aliphatic polyisocyanate compounds generally provide better light stability than the aromatic compounds. Aromatic polyisocyanate compounds, on the other hand, are generally more economical and reactive toward nucleophiles than are aliphatic polyisocyanate compounds. Suitable aromatic polyisocyanate compounds include, but are not limited to, those selected from the group consisting of 2,4-toluene diisocyanate (TDI), 2,6-toluene diisocyanate, an adduct of TDI with trimethylolpropane (available as Desmodur™ CB from Bayer Corporation, Pittsburgh, Pa.), the isocyanurate trimer of TDI (available as Desmodur™ IL from Bayer Corporation, Pittsburgh, Pa.), diphenylmethane 4,4'-diisocyanate (MDI), diphenylmethane 2,4'-diisocyanate, 1,5-diisocyanato-naphthalene, 1,4-phenylene diisocyanate, 1,3-phenylene diisocyanate, 1-methoxy-2,4-phenylene diisocyanate, 1-chlorophenyl-2,4-diisocyanate, and mixtures thereof.

Examples of useful alicyclic polyisocyanate compounds include, but are not limited to, those selected from the group consisting of dicyclohexylmethane diisocyanate ($H_{12}$MDI, commercially available as Desmodur™ available from Bayer Corporation, Pittsburgh, Pa.), 4,4'-isopropyl-bis(cyclohexyl-isocyanate), isophorone diisocyanate (IPDI), cyclobutane-1,3-diisocyanate, cyclohexane 1,3-diisocyanate, cyclohexane 1,4-diisocyanate (CHDI), 1,4-cyclohexanebis(methylene isocyanate) (BDI), dimer acid diisocyanate (available from Bayer), 1,3-bis(isocyanatomethyl)cyclohexane ($H_6$XDI), 3-isocyanatomethyl-3,5,5-trimethylcyclohexyl isocyanate, and mixtures thereof.

Examples of useful aliphatic polyisocyanate compounds include, but are not limited to, those selected from the group consisting of tetramethylene 1,4-diisocyanate, hexamethylene 1,4-diisocyanate, hexamethylene 1,6-diisocyanate (HDI), octamethylene 1,8-diisocyanate, 1,12-diisocyanatododecane, 2,2,4-trimethyl-hexamethylene diisocyanate (TMDI), 2-methyl-1,5-pentamethylene diisocyanate, dimer diisocyanate, the urea of hexamethylene diisocyanate, the biuret of hexamethylene 1,6-diisocyanate (HDI) (Desmodur™ N-100 and N-3200 from Bayer Corporation, Pittsburgh, Pa.), the isocyanurate of HDI (available as Desmodur™ N-3300 and Desmodur™ N-3600 from Bayer Corporation, Pittsburgh, Pa.), a blend of the isocyanurate of HDI and the uretdione of HDI (available as Desmodure™ N-3400 available from Bayer Corporation, Pittsburgh, Pa.), and mixtures thereof.

Examples of useful aralkyl polyisocyanates include, but are not limited to, those selected from the group consisting of m-tetramethyl xylylene diisocyanate (m-TMXDI), p-tetramethyl xylylene diisocyanate (p-TMXDI), 1,4-xylylene diisocyanate (XDI), 1,3-xylylene diisocyanate, p-(1-isocyanatoethyl)phenyl isocyanate, m-(3-isocyanatobutyl)phenyl isocyanate, 4-(2-isocyanatocyclohexyl-methyl)phenyl isocyanate, and mixtures thereof.

Preferred polyisocyanates, in general, include those selected from the group consisting of tetramethylene 1,4-diisocyanate, hexamethylene 1,4-diisocyanate, hexamethylene 1,6-diisocyanate (HDI), octamethylene 1,8-diisocyanate, 1,12-diisocyanatododecane, mixtures thereof, and a biuret, an isocyanurate, or a uretdione derivatives.

The fluorochemical urethane comprises, in part, the reaction product of a fluorinated compound having a mono- or difunctional perfluorinated group, and at least one nucleophilic, isocyanate-reactive functional group (herein a "nucleophilic fluorinated compound"). Such compounds include those of the formula:

where $R_f^1$ is a monovalent perfluoroalkyl or a perfluorooxyalkyl group, or a divalent perfluoroalkylene or a perfluorooxyalkylene group, Q is a covalent bond, or a polyvalent alkylene group of valency z, said alkylene optionally containing one or more catenary (in-chain) nitrogen or oxygen atoms, and optionally containing one or more sulfonamide, carboxamido, or carboxy functional groups, $X^2$ is —O—, —$NR^4$— or —S—, where $R^4$ is H or $C_1$-$C_4$ alkyl, y is 1 or 2, and z is independently 1 or 2.

With respect to Formulas I and III, the reaction between the nucleophilic fluorinated compound (III) and an isocyanate group of a polyisocyanate produces a group of the formula

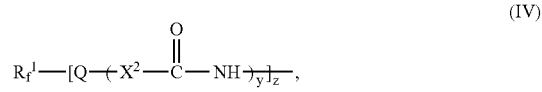

where $R_f^1$, Q, $X^2$, y and z are as previously defined for Formula III.

The $R_f^1$ groups of Formula III and IV can contain straight chain, branched chain, or cyclic fluorinated groups or any combination thereof, and can be mono- or divalent. The $R_f^1$ groups can optionally contain one or more catenary oxygen atoms in the carbon-carbon chain so as to form a carbon-oxygen-carbon chain (i.e. a oxyalkylene group). Fully-fluorinated groups are generally preferred, but hydrogen or chlorine atoms can also be present as substituents, provided that no more than one atom of either is present for every two carbon atoms.

It is additionally preferred that any $R_f^1$ group contain at least about 40% fluorine by weight, more preferably at least about 50% fluorine by weight. The terminal portion of the monovalent $R_f^1$ group is generally fully-fluorinated, preferably containing at least three fluorine atoms, e.g., $CF_3—$, $CF_3CF_2—$, $CF_3CF_2CF_2—$, $(CF_3)_2N—$, $(CF_3)_2CF—$, $SF_5CF_2—$. In certain embodiments, monovalent perfluoroalkyl groups (i.e., those of the formula $C_nF_{2n+1}—$) or divalent perfluoroalkylene groups (i.e., those of the formula $—C_nF_{2n}—$) wherein n is 2 to 12 inclusive are the preferred $R_f^1$ groups, with n=3 to 5 being more preferred and with n=4 being the most preferred.

Useful perfluorooxyalkyl and perfluorooxyalkylene groups correspond to the formula:

$$R_f^6 \cdot R_f^3—O—R_f^4—(R_f^5)_q— \qquad (V)$$

wherein $R_f^6$ is F (fluorine) for monovalent perfluorooxyalkyl, and an open valence ("-") for divalent perfluorooxyalkylene;

$R_f^3$ represents a perfluoroalkylene group, $R_f^4$ represents a perfluoroalkyleneoxy group consisting of perfluoroalkyleneoxy groups having 1, 2, 3 or 4 carbon atoms or a mixture of such perfluoroalkyleneoxy groups, $R_f^5$ represents a perfluoroalkylene group and q is 0 or 1. The perfluoroalkylene groups $R_f^3$ and $R_f^5$ in formula (IV) may be linear or branched and may comprise 1 to 10 carbon atoms, preferably 1 to 6 carbon atoms. A typical monovalent perfluoroalkyl group is $CF_3—CF_2—CF_2—$ and a typical divalent perfluoroalkylene is $—CF_2—CF_2—CF_2—$, $—CF_2—$ or $—CF(CF_3)—$. Examples of perfluoroalkyleneoxy groups $R_f^4$ include: $—CF_2—CF_2—O—$, $—CF(CF_3)—CF_2—O—$, $—CF_2—CF(CF_3)—O—$, $—CF_2—CF_2—CF_2—O—$, $—CF_2—O—$, $—CF(CF_3)—O—$, and $—CF_2—CF_2—CF_2—CF_2—O$, which may repeat, for example, from 3 to 30 times.

The perfluoroalkyleneoxy group $R_f^4$ may be comprised of the same perfluorooxyalkylene units or of a mixture of different perfluorooxyalkylene units. When the perfluorooxyalkylene group is composed of different perfluoroalkylene oxy units, they can be present in a random configuration, alternating configuration or they can be present as blocks. Typical examples of perfluorinated poly(oxyalkylene) groups include: $—[CF_2—CF_2—O]_r—$; $—[CF(CF_3)—CF_2—O]_s—$; $—[CF_2CF_2—O]_r—[CF_2O]_t—$, $—[CF_2CF_2CF_2CF_2—O]_u$ and $—[CF_2—CF_2—O]_r—[CF(CF_3)—CF_2—O]_s—$; wherein each of r, s, t and u each are integers of 1 to 50, preferably 2 to 25. A preferred perfluorooxyalkyl group that corresponds to formula (V) is $CF_3—CF_2—CF_2—O—[CF(CF_3)—CF_2O]_s—CF(CF_3)CF_2—$ wherein s is an integer of 1 to 50.

Perfluorooxyalkylene and perfluorooxyalkyl compounds can be obtained by oligomerization of hexafluoropropylene oxide that results in a terminal carbonyl fluoride group. This carbonyl fluoride may be converted into an acid, ester or alcohol by reactions well known to those skilled in the art. The carbonyl fluoride or acid, ester or alcohol derived therefrom may be reacted further to introduce the desired isocyanate reactive groups according to known procedures.

With respect to Formula I to III, where x or z is 1, nucleophilic fluorochemical monofunctional compounds, such as monoalcohols and monoamines are contemplated. Representative examples of useful fluorochemical monofunctional compounds include the following:

$CF_3(CF_2)_3SO_2N(CH_3)CH_2CH_2OH$, $CF_3(CF_2)_3SO_2N(CH_3)CH(CH_3)CH_2OH$, $CF_3(CF_2)_3SO_2N(CH_3)CH_2CH(CH_3)NH_2$, $CF_3(CF_2)_3SO_2N(CH_2CH_3)CH_2CH_2SH$, $CF_3(CF_2)_3SO_2N(CH_3)CH_2CH_2SCH_2CH_2OH$, $C_6F_{13}SO_2N(CH_3)(CH_2)_4OH$, $CF_3(CF_2)_7SO_2N(H)(CH_2)_3OH$, $C_3F_7SO_2N(CH_3)CH_2CH_2OH$, $CF_3(CF_2)_4SO_2N(CH_3)(CH_2)_4NH_2$, $C_4F_9SO_2N(CH_3)(CH_2)_{11}OH$, $CF_3(CF_2)_5SO_2N(CH_2CH_3)CH_2CH_2OH$, $CF_3(CF_2)_5SO_2N(C_2H_5)(CH_2)_6OH$, $CF_3(CF_2)_2SO_2N(C_2H_5)(CH_2)_4OH$, $CF_3(CF_2)_3SO_2N(C_3H_7)CH_2OCH_2CH_2OH$, $CF_3(CF_2)_4SO_2N(CH_2CH_2CH_3)CH_2CH_2OH$, $CF_3(CF_2)_4SO_2N(CH_2CH_2CH_3)CH_2CH_2NHCH_3$, $CF_3(CF_2)_3SO_2N(C_4H_9)CH_2CH_2NH_2$, $CF_3(CF_2)_3SO_2N(C_4H_9)(CH_2)_4SH$, $CF_3(CF_2)_3CH_2CH_2OH$, $C_4F_9OC_2F_4OCF_2CH_2OCH_2CH_2OH$; $n-C_6F_{13}CF(CF_3)CON(H)CH_2CH_2OH$; $C_6F_{13}CF(CF_3)CO_2C_2H_4CH(CH_3)OH$; $C_3F_7CON(H)CH_2CH_2OH$; $C_3F_7O(CF(CF_3)CF_2O)_{1-36}CF(CF_3)CH_2OH$;

and the like, and mixtures thereof. If desired, other isocyanate-reactive functional groups may be used in place of those depicted.

With respect to Formulas I to III, where x or z is 2, fluorinated polyols are preferred. Representative examples of suitable fluorinated polyols include $R_f^1SO_2N(CH_2CH_2OH)_2$ such as N-bis(2-hydroxyethyl)perfluorobutylsulfonamide; $R_f^1OC_6H_4SO_2N(CH_2CH_2OH)_2$; $R_f^1SO_2N(R')CH_2CH(OH)CH_2OH$ such as $C_6F_{13}SO_2N(C_3H_7)CH_2CH(OH)CH_2OH$; $R_f^1CH_2CON(CH_2CH_2OH)_2$; $R_f^1CON(CH_2CH_2OH)_2$; $CF_3CF_2(OCF_2CF_2)_3OCF_2CON(CH_3)CH_2CH(OH)CH_2OH$; $R_f^1OCH_2CH(OH)CH_2OH$ such as $C_4F_9OCH_2CH(OH)CH_2OH$; $R_f^1CH_2CH_2SC_3H_6OCH_2CH(OH)CH_2OH$; $R_f^1CH_2CH_2SC_3H_6CH(CH_2OH)_2$; $R_f^1CH_2CH_2SCH_2CH(OH)CH_2OH$; $R_f^1CH_2CH_2SCH(CH_2OH)CH_2CH_2OH$; $R_f^1CH_2CH_2CH_2SCH_2CH(OH)CH_2OH$ such as $C_5F_{11}(CH_2)_3SCH_2CH(OH)CH_2OH$; $R_f^1CH_2CH_2CH_2OCH_2CH(OH)CH_2OH$ such as $C_5F_{11}(CH_2)_3OCH_2CH(OH)CH_2OH$; $R_f^1CH_2CH_2CH_2OC_2H_4OCH_2CH(OH)CH_2OH$; $R_f^1CH_2CH_2(CH_3)OCH_2CH(OH)CH_2OH$; $R_f^1(CH_2)_4SC_3H_6(CH_2OH)CH_2OH$; $R_f^1(CH_2)_4SCH_2CH(CH_2OH)_2$; $R_f^1(CH_2)_4SC_3H_6OCH_2CH(OH)CH_2OH$; $R_f^1CH_2CH(C_4H_9)SCH_2CH(OH)CH_2OH$; $R_f^1CH_2OCH_2CH(OH)CH_2OH$; $R_f^1CH_2CH(OH)CH_2SCH_2CH_2OH$; $R_f^1CH_2CH(OH)CH_2SCH_2CH_2OH$; $R_f^1CH_2CH(OH)CH_2OCH_2CH_2OH$; $R_f^1CH_2CH(OH)CH_2OH$; $R_f^1R"SCH(R"'OH)CH(R"'OH)SR'R_f$; $(R_f^1CH_2CH_2SCH_2CH_2SCH_2)_2C(CH_2OH)_2$; $((CF_3)_2CFO(CF_2)_2C(CH_2OH)_2$; $(R_f^1R"SCH_2)_2C(CH_2OH)_2$; 1,4-bis(1-hydroxy-1,1-dihydroperfluoroethoxyethoxy)perfluoro-n-butane $(HOCH_2CF_2OC_2F_4O(CF_2)_4OC_2F_4OCF_2CH_2OH)$; 1,4-bis(1-hydroxy-1,1-dihydroperfluoropropoxy)perfluoro-n-butane $(HOCH_2CF_2CF_2O(CF_2)_4OCF_2CF_2CH_2OH)$; fluorinated oxetane polyols made by the ring-opening polymerization of fluorinated oxetane such as Poly-3-Fox™ (available from Omnova Solutions, Inc., Akron Ohio); polyetheralcohols prepared by ring opening addition polymerization of a fluorinated organic group substituted epoxide with a compound containing at least two hydroxyl groups as described in U.S. Pat. No. 4,508,916 (Newell et al); and perfluoropolyether diols such as Fomblin™ ZDOL $(HOCH_2CF_2O(CF_2O)_{8-12}(CF_2CF_2O)_{8-12}CF_2CH_2OH$, available from Ausimont);

wherein $R_f^1$ is a perfluoroalkyl group having 1 to 12 carbon atoms, or a perfluorooxyalkyl group having 3 to about 50 carbon atoms with all perfluorocarbon chains present having 6 or fewer carbon atoms, or mixtures thereof, R' is alkyl of 1 to 4 carbon atoms; R" is branched or straight chain alkylene of 1 to 12 carbon atoms, alkylenethio-alkylene of 2 to 12 carbon atoms, alkylene-oxyalkylene of 2 to 12 carbon atoms, or alkylene iminoalkylene of 2 to 12 carbon atoms, where the nitrogen atom contains as a third substituent hydrogen or alkyl of 1 to 6 carbon atoms; and R''' is a straight or branched chain alkylene of 1 to 12 carbon atoms or an alkylene-polyoxyalkylene of formula $C_rH_{2r}(OC_sH_{2s})_t$ where r is 1-12, s is 2-6, and t is 1-40.

Preferred fluorinated polyols include N-bis(2-hydroxyethyl) perfluorobutylsulfonamide; fluorinated oxetane polyols made by the ring-opening polymerization of fluorinated oxetane such as Poly-3-Fox™ (available from Omnova Solutions, Inc., Akron Ohio); polyetheralcohols prepared by ring opening addition polymerization of a fluorinated organic group substituted epoxide with a compound containing at least two hydroxyl groups as described in U.S. Pat. No. 4,508,916 (Newell et al); perfluoropolyether diols such as Fomblin™ ZDOL ($HOCH_2CF_2O(CF_2O)_{8-12}(CF_2CF_2O)_{8-12}CF_2CH_2OH$, available from Ausimont); 1,4-bis(1-hydroxy-1,1-dihydroperfluoroethoxyethoxy)perfluoro-n-butane ($HOCH_2CF_2OC_2F_4O(CF_2)_4OC_2F_4OCF_2CH_2OH$); and 1,4-bis(1-hydroxy-1,1-dihydroperfluoropropoxy)perfluoro-n-butane ($HOCH_2CF_2CF_2O(CF_2)_4 OCF_2CF_2CH_2OH$).

More preferred polyols comprised of at least one fluorine-containing group include N-bis(2-hydroxyethyl)perfluorobutylsulfonamide; 1,4-bis(1-hydroxy-1,1-dihydroperfluoropropoxy)perfluoro-n-butane ($HOCH_2CF_2CF_2O(CF_2)_4 OCF_2CF_2CH_2OH$) and $CF_3CF_2CF_2$—O—$[CF(CF_3)CF_2O]_{3-25}$—$CF(CF_3)$—. This perfluorinated polyether group can be derived from an oligomerization of hexafluoropropylene oxide. Such perfluorinated polyether groups are preferred in particular because of their benign environmental properties.

The compounds of Formula I comprise one or more water solubilizing groups or groups capable of forming water-solubilizing groups so as to obtain a repellent additive that can more easily be dispersed in water. Suitable water solubilizing groups include cationic, anionic and zwitterionic groups as well as non-ionic water solubilizing groups.

The fluorochemical compounds may further comprise, in part, the free-radical addition reaction product of water-solubilizing compounds comprising one or more water-solubilizing groups and at least one thiol group. The water-solubilizing compounds can be represented by the Formula:

$$HS-R^5-(W^1)_w, \quad (VI)$$

wherein $R^5$ is a divalent alkylene group, said alkylene groups optionally containing one or more catenary oxygen atoms, $W^1$ is a water-solubilizing group, and w is 1 to 3.

The water-solubilizing groups of the water solubilizing compounds improve the aqueous solubility or dispersibility and include, for example, hydroxy, carboxylate, sulfate, sulfonate, phosphate, phosphonate, ammonium, and quaternary ammonium groups. Such groups may be represented as —$CO_2M$, —OH, —$OSO_3M$, —$SO_3M$, —$PO(OM)_2$, —$P(OM)_3$, —$NR^8_2HX$, —$NR^8_3X$, —$NR^8H_2X$, and —$NH_3X$, respectively, wherein M is H or one equivalent of a monovalent or divalent soluble cation such as sodium, potassium, calcium, and $N(R^4)_3H+$, where $R^4$ is H or $C_1$-$C_4$ alkyl; X is a soluble anion such as those selected from the group consisting of halide, hydroxide, carboxylate, sulfonates, and the like; and $R^8$ is selected from the group consisting of a phenyl group, a cycloaliphatic group, or a straight or branched aliphatic group having from about 1 to about 12 carbon atoms. Preferably, $R^8$ is a lower alkyl group having from 1 to 4 carbon atoms. The group —$NR^8_3X$ is a salt of a water-soluble acid, for example trimethyl ammonium chloride, pyridinium sulfate, etc. or an ammonium substituent. The group —$NR^8_2HX$ is the salt of a water-soluble acid, such as dimethyl ammonium acetate or propionate. The group —$NR^8H_2X$ is the salt of a water-soluble acid, such as methyl ammonium acetate or propionate. The group —$NH_3X$ is the salt of a water-soluble acid, such as ammonium acetate or propionate. The salt form can be made by simple neutralization of the acid group with a base such as an amine, a quaternary ammonium hydroxide, an alkali metal carbonate or hydroxide, or the like; or alternatively by simple reaction of the amino group with a carboxylic acid, a sulfonic acid, a halo acid, or the like.

Illustrative ionic water-solubilizing compounds having suitable water-solubilizing groups include, but are not limited to, those independently selected from the group consisting of $HSCH_2COOH$; $HSCH_2CH_2OH$; $(HSCH_2CH_2)_2NCH_2COOH$; $HSC(CO_2H)(CH_2CO_2H)_2$; $(HS(CH_2)_nCH_2)_2NCH_3$ wherein n is an integer of 1 to 3; $(HSCH_2)_2C(CH_3)COOH$; $(HS(CH_2)_nCH_2)_2NCH_3$ wherein n is an integer of 1 to 3; $HSCH_2CH(OH)CO_2Na$; $(HSCH_2CH_2N(CH_2COOH)_2)$; $(HSCH(COOH)(CH_2CH_2COOH))$; $(HSCH(COOH)(CH_2COOH))$; $(HSCH_2COOH)$; $(HSCH(CH_2N(CH_2COOH)_2)_2)$; $HSCH(COOH)(CH_2COOH)$; $HS(CH_2)_4CH(COOH)N(CH_2COOH)_2$; $HSCH(COOH)CH(COOH)CH_2COOH$; $(HSCH_2)_2CHCH_2COO)^-(NH(CH_3)_3)^+$; $HSCH_2CH_2OSO_3Na$; $HSC_2H_4NHC_2H_4SO_3H$; $HSC_3H_6NH(CH_3)C_3H_6SO_3H$; $(HSC_2H_4)_2NC_3H_6OSO_3Na$; $(HSCH_2CH_2)_2NC_6H_4OCH_2CH_2OSO_2OH$; $(HSC_6H_4SO_3)^-(NH(C_2H_5)_3)^+$; and salts of the above amines, carboxylic acids, and sulfonic acids.

The fluorochemical urethane compounds comprise, in part, the reaction product of a nucleophilic ethylenically unsaturated compound having an isocyanate-reactive, nucleophilic functional group and least one ethylenically unsaturated group (hereinafter a "nucleophilic unsaturated compound"). The unsaturated group may be a vinyl, allyl or allyloxy and the nucleophilic functional group may be an amino or hydroxy group. Preferably the unsaturated group is not a vinyloxy group, e.g. $CH_2$=CHO—. Preferably, the nucleophilic unsaturated compound is a polyunsaturated compound having a hydroxyl group and at least two unsaturated groups.

Such compounds include those of the formula:

$$HX^1-R^3-(CH=CH_2)_q, \quad (VII)$$

wherein $X^1$ is —O— or —$NR^4$—, where $R^4$ is H or $C_1$-$C_4$ alkyl, $R^3$ is a divalent alkylene or arylene groups, or combinations thereof, said alkylene groups optionally containing one or more catenary oxygen atoms; and q is 1 to 5.

Preferably q is greater than 1. The resulting nucleophilic polyunsaturated compounds allow the addition of multiple silane groups to the urethane compound. The molar ratio of silane groups and water-solubilizing groups to —NH—C(O)—$X^1$— groups may be greater than 1:1, or greater than 2:1. Preferably $HX^1$— is not directly connected to an aromatic ring, such as with a phenolic compound.

Compounds of Formula VII include terminally mono-, di- or poly-unsaturated ethers of polyols such as 1,3-butylene glycol, 1,4-butanediol, 1,6-hexanediol, cyclohexane dimethanol, neopentyl glycol, caprolactone modified neopentylglycol hydroxypivalate, diethylene glycol, dipropylene glycol, bisphenol-A, trimethylolpropane, neopentyl glycol, tetraethylene glycol, tricyclodecanedimethanol, triethylene glycol, tripropylene glycol; glycerol, pentaerythritol, and dipentaerythritol pentaacrylate.

Useful nucleophilic unsaturated compounds include hydroxyalkenes such as allyl alcohol, methallyl alcohol, allyloxyethyl alcohol, 2-allyloxymethylpropanol (from dimethylolethane), and 2,2-di(allyloxymethyl)butanol (from trimethylolpropane), as well as the corresponding amines.

The nucleophilic unsaturated compound (VII) may react with a portion of the isocyanate groups of the polyisocyanate to form a urethane compound having pendent unsaturated groups (VIII below), which may subsequently be reacted with a thiosilane (below) and water-solubilizing compound (VI) to form a compound of Formula I.

The reaction product of the nucleophilic unsaturated compound with the isocyanate is of the general formula:

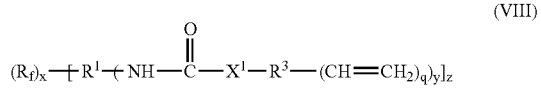
(VIII)

wherein $R_f$ is a fluorine-containing group, comprising a monovalent perfluoroalkyl or a perfluorooxyalkyl group, or a divalent perfluoroalkylene or a perfluorooxyalkylene group, $R^1$ is the residue of a polyisocyanate, $X^1$ is —O— or —NR$^4$—, where $R^4$ is H or $C_1$-$C_4$ alkyl, $R^3$ is a divalent alkylene or arylene groups, or combinations thereof, said alkylene groups optionally containing one or more catenary oxygen atoms;

x is 1 or 2;

y is at least 1;

z is independently 1 or 2, and q is 1 to 5, preferably 2 to 5.

The fluorochemical urethane compounds comprise, in part, the free radical addition reaction product of a thiosilane with an unsaturated group of the compounds of Formulas VII or VIII.

The thiosilane is of the formula

(IX)

wherein $R^5$ is a divalent alkylene group, said alkylene groups optionally containing one or more catenary oxygen atoms;

Y is a hydrolysable group, $R^6$ is a monovalent alkyl or aryl group, and p is 1, 2 or 3.

Y represents a hydrolysable group in Formula (VIII) such as for example a halide, a $C_1$-$C_4$ alkoxy group, an acyloxy group or a polyoxyalkylene group, such as polyoxyethylene groups as disclosed in U.S. Pat. No. 5,274,159. By hydrolysable it is meant the Y group will undergo an exchange reaction with water to form a Si—OH moiety, which may further react to form siloxane groups. Specific examples of hydrolysable groups include methoxy, ethoxy and propoxy groups, chlorine and an acetoxy group. $R^6$ is generally non-hydrolyzable.

The thiosilane (IX) and/or water-solubilizing compound (VI) may be reacted with the nucleophilic unsaturated compound VII or to form an addition product, which may subsequently be reacted with the polyisocyanate (either before or after functionalization by the nucleophilic fluorinated compound III). Alternatively, the nucleophilic unsaturated compound of Formula VII may first be reacted with a polyisocyanate to form a urethane compound of Formula VIII, followed by free-radical addition of the thiosilane (IX) and the water-solubilizing compound (VI) to the ethylenically unsaturated groups pendent from the urethane compound. Preferably, the nucleophilic unsaturated compound (VII) is first reacted with the polyisocyanate (again, before or after reaction with the nucleophilic fluorinated compound III), to form a urethane compound having pendent unsaturated groups, to which is added the thiosilane (IX) and the water-solubilizing compound (VI) by free radical addition. The general reaction schemes are shown below:

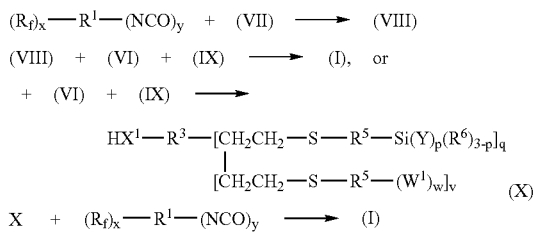

Useful thiosilanes include (mercaptomethyl)dimethylethoxysilane, (mercaptomethyl)methyldiethoxysilane, 3-mercaptopropylmethyldimethoxysilane, 3-mercaptopropyltriethoxysilane(mercaptomethyl)methyldiethoxysilane.

The addition of the thiosilane (IX) and the water-solubilizing compound (V) to either of the ethylenically unsaturated compounds (VII or VIII) may be effected using free radical initiators. Useful free radical initiators include inorganic and organic peroxides, hydroperoxides, persulfates, azo compounds, redox systems (e.g., a mixture of $K_2S_2O_8$ and $Na_2S_2O_5$), and free radical photoinitiators such as those described by K. K. Dietliker in Chemistry & Technology of UV & EB Formulation for Coatings, Inks & Paints, Volume 3, pages 276-298, SITA Technology Ltd., London (1991). Representative examples include hydrogen peroxide, potassium persulfate, t-butyl hydroperoxide, benzoyl peroxide, t-butyl perbenzoate, cumene hydroperoxide, 2,2'-azobis(2-methylbutyronitrile), (VAZO 67) and azobis(isobutyronitrile) (AIBN). The skilled artisan will recognize that the choice of initiator will depend upon the particular reaction conditions, e.g., choice of solvent.

It will be understood that the free-radical addition of the thiosilane can add to either the least or more substituted carbon atom of the ethylenically unsaturated group, and addition to the less substituted carbon is illustrated in the Figures for convenience. Thus:

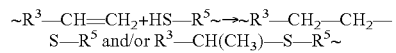

The fluorochemical compounds can be made by simple blending of the nucleophilic unsaturated compound(s), fluorine-containing nucleophilic compound(s), and the polyisocyanate compound(s), followed by free-radical addition of the thiosilanes (IX) and/or the water-solubilizing compounds (VI) to the unsaturated groups. As one skilled in the art would understand, the order of blending or the ordering of the steps is non-limiting and can be modified so as to produce a desired fluorochemical urethane compounds. In one embodiment, for example, the polyisocyanate compound(s), and the nucleophilic fluorochemical compound (III) are first reacted with some portion of the isocyanate groups, followed by reaction with the nucleophilic unsaturated compound (VII) with all or a portion of the remaining isocyanate groups, followed by free-radical addition of the thiosilane (IX) and the water-solubilizing compounds (VI) to the pendent unsaturated groups.

In general, the nucleophilic reactive components, the polyisocyanate and a solvent are charged to a dry reaction vessel together, in immediate succession, or as pre-made mixtures. When a homogeneous mixture or solution is obtained a catalyst is optionally added, and the reaction mixture is heated at a temperature, and for a time sufficient for the reaction to occur. Progress of the reaction can be determined by monitoring the disappearance of the isocyanate peak in the IR.

In general, the nucleophilic fluorinated compound $R_f$—Q $(X^2H)_z$ (III), is used in an amount sufficient to react with 5 to 50 mole percent of the available isocyanate functional groups. Preferably, compound III is used to react with 10 to 30 mole percent of the isocyanate groups. The remaining isocyanate groups, about 50 to 95 mole percent, preferably 70 to 90 mole percent is functionalized by the nucleophilic unsaturated compound (VII), followed by free radical addition of the thiosilane (IX) and/or the water-solubilizing compounds (VI), or alternatively by the reaction product of compounds of Formula VII (VI) and (IX), resulting in a urethane compound of Formula I having both pendent fluorochemical groups, pendent water-solubilizing and pendent silane groups.

Preferably, the ratio of the total number of equivalents of nucleophilic groups (of both the fluorine-containing nucleophilic compounds and nucleophilic unsaturated compounds) to the total number of equivalents of isocyanate groups is about 1:1, i.e. that all or essentially all of the isocyanate groups are reacted.

Depending on reaction conditions (e.g., reaction temperature and/or polyisocyanate used), a catalyst level of up to about 0.5 percent by weight of the reaction mixture may be used may be used to effect the isocyanate condensation reaction, but typically about 0.00005 to about 0.5 percent by weight may be used, 0.02 to 0.1 percent by weight being preferred. In general, if the nucleophilic group is an amine group, a catalyst is not necessary.

Suitable catalysts include, but are not limited to, tertiary amine and tin compounds. Examples of useful tin compounds include tin II and tin IV salts such as stannous octoate, dibutyltin dilaurate, dibutyltin diacetate, dibutyltin di-2-ethylhexanoate, and dibutyltinoxide. Examples of useful tertiary amine compounds include triethylamine, tributylamine, triethylenediamine, tripropylamine, bis(dimethylaminoethyl) ether, morpholine compounds such as ethyl morpholine, and 2,2'-dimorpholinodiethyl ether, 1,4-diazabicyclo[2.2.2]octane (DABCO), and 1,8-diazabicyclo[5.4.0.]undec-7-ene (DBU). Tin compounds are preferred. If an acid catalyst is used, it is preferably removed from the product or neutralized after the reaction. It has been found that the presence of the catalyst may deleteriously affect the contact angle performance.

The fluorochemical compositions of the present invention comprising a mixture of urethane molecules can also be made following a step-wise synthesis, in addition to a batch method. In the synthesis, the polyisocyanate and the fluorinated nucleophilic compound(s) are dissolved together under dry conditions, preferably in a solvent, and then the resulting solution is heated at a temperature sufficient to effect the condensation reaction, optionally in the presence of a catalyst. Pendent fluorine-containing groups are thereby bonded to the isocyanate functional urethane oligomers and compounds.

The resulting isocyanate fluorochemical functional urethane compounds are then further reacted with one or more of the nucleophilic unsaturated compounds (VII) described above, which added to the above reaction mixture, and react(s) with the remaining or a substantial portion of the remaining isocyanate groups, resulting in a urethane compound having both pendent fluorochemical groups and pendent unsaturated groups, the unsaturated groups of which may be further functionalized by free-radical addition of the thiosilanes (IX) and the water-solubilizing compounds (VI).

Compositions according to the present invention may be coated on a substrate and at least partially cured to provide a coated article. In some embodiments, the polymerized coating may form a protective coating that provides at least one of mar resistance, graffiti resistance, stain resistance, adhesive release, low refractive index, and water repellency. Coated articles according to the present invention include, for example, eyeglass lenses, mirrors, windows, adhesive release liners, and anti-graffiti films.

Suitable substrates include, for example, glass (e.g., windows and optical elements such as, for example, lenses and mirrors), ceramic (e.g., ceramic tile), cement, stone, painted or clearcoated surfaces (e.g., automobile body panels, boat surfaces), metal (e.g., architectural columns), paper (e.g., adhesive release liners), cardboard (e.g., food containers), thermosets, thermoplastics (e.g., polycarbonate, acrylics, polyolefins, polyurethanes, polyesters, polyamides, polyimides, phenolic resins, cellulose diacetate, cellulose triacetate, polystyrene, and styrene-acrylonitrile copolymers), and combinations thereof. The substrate may be a film, sheet, or it may have some other form. The substrate may comprise a transparent or translucent display element, optionally having a ceramer or silsesquioxane hardcoat thereon.

In some embodiments, a coating composition comprising a mixture of the fluorochemical urethane compounds and water or a solvent is provided. The coating compositions of the present invention comprise solvent or water suspensions, dispersions or solutions of the fluorochemical compounds of the present invention. When applied as coatings, the coating compositions impart oleophobic, hydrophilic, and antisoiling characteristics to any of a wide variety of substrates.

"Oleophobic" means repelling or tending not to combine with oil or grease; and "hydrophilic" means having a strong tendency to bind or absorb water. Accordingly, the compounds of Formula I, when applied to a substrate, lowers the surface tension thereof to the extent that the substrate will exhibit a receding contact angle with water of less than about 60°, preferably less than about 50°, and most preferably less than 45°; and a receding contact angle with n-hexadecane of at least 20°, preferably at least 25°, and most preferably at least 30° measured after drying and curing of the coating. An oleophobic surface will resist or retard soiling, and a hydrophilic surface will allow water to "sheet-out" on a surface.

The fluorochemical compounds can be dissolved, suspended, or dispersed in water to form coating compositions suitable for use in coating onto a substrate. Generally, the coating compositions can contain from about 0.1 to about 50 weight percent, or even up to about 90 percent non-volatile solids (based on the total weight of the components). Preferably, the coating composition contains about 1 to 10 percent total solids. More preferably the amount of fluorochemical urethane compounds used in the coating is about 0.1 to about 5 weight percent solids.

For solvent solutions, suitable solvents include alcohols, esters, glycol ethers, amides, ketones, hydrocarbons, hydrofluorocarbons, hydrofluoroethers, chlorohydrocarbons, chlorocarbons, and mixtures thereof.

For ease of manufacturing and for reasons of cost, the compositions of the present invention can be prepared shortly before use by diluting a concentrate of one or more of the fluorinated polyether isocyanate derived silanes. The concentrate will generally comprise a concentrated solution of the compounds of Formula I in an organic solvent. The concentrate should be stable for several weeks, preferably at least 1 month, more preferably at least 3 months. It has been found that the fluorinated isocyanate derived silane can be readily dissolved in an organic solvent at high concentrations.

In some embodiments, the coating composition comprises an aqueous dispersion, solution or suspension of the urethane compounds of Formula I. As result of the high concentration of silyl groups, as when "q" of Formula II is two or greater, and water-solubilizing groups, the compounds are readily suspended in water. These aqueous coating compositions may be prepared by "inverting" an organic solvent solution of the compounds into water by adding to water, with agitation, optionally containing a surfactant, and removing the organic solvent under reduced pressure, with agitation. High shear mixing is a preferred means of agitation the suspensions.

Surfactants useful in the preparation of emulsions include the categories of anionic, nonionic, and amphoteric surfactants. Cationic surfactants are generally not useful due to the deleterious effect on the silane and siloxane groups. Useful anionic surfactants include but are not limited to sulfosuccinates and derivatives, alkylaryl sulfonates, olefin sulfonates, phosphate esters, sulfates and sulfonates of ethoxylated alkylphenols, sulfates and sulfonates of ethoxylated fatty alcohols, sulfates of fatty esters, and mixtures thereof. Useful nonionic surfactants include but are not limited to the following: ethoxylated fatty alcohols, ethoxylated fatty esters, ethoxylated fatty acids, ethoxylated alkylphenols, ethylene oxide-propylene oxide block copolymers, and mixtures thereof. Useful amphoteric surfactants include but are not limited to the following: betaine derivatives, sulfobetaine derivatives, and mixtures thereof.

In addition to water, the compositions of the invention may also include an organic or inorganic acid. Organic acids include acetic acid, citric acid, formic acid and the like; fluorinated organic acids, such as $CF_3SO_3H$, $C_3F_7CO_2K$ or those which can be represented by the formula $R_f^2[-(L)_3-Z]_b$, wherein $R_f^2$ represents a mono perfluoroalkyl or perfluorooxy or divalent perfluoroalkylene or perfluoroalkyleneoxy group, L represents an organic divalent linking group, Z represents an acid group, such as carboxylic, sulfonic or phosphonic acid group; a is 0 or 1 and b is 1 or 2.

Examples of suitable $R_f^2$ groups include those given above for $R_f$. Examples of organic acids of formula (IV) include $C_3F_7O(CF(CF_3)CF_2)_{10-30}CF(CF_3)COOH$, commercially available from DuPont or $CF_3(CF_2)_2OCF(CF_3)COOH$. Examples of inorganic acids include sulfuric acid, hydrochloric acid and the like. The acid will generally be included in the composition in an amount between about 0.01 and 10%, more preferably between 0.05 and 5% by weight, relative to the weight of the silane.

The acid may be formulated into the coating composition per se, or subsequent to coating with the perfluoropolyether silane, the coated substrate may be dipped in an acid solution to effect the formation of a siloxane layer.

The coating composition may further comprise aminosilanes, which have been found to substantially increase the durability of the coating. In general, the amino silanes can be added at 0.1 to 25 wt. %, relative to the total solid of the coating composition. Above this limit, Applicants observe increased haze/loss of gloss in the coating and below this limit the abrasion resistance is less. Preferably the aminosilane is used at 1 to 10 wt. %, most preferably 2 to 7 wt. %. Small amounts of isopropanol or another suitable solvents may be added to improve the stability of the aminosilane.

Useful aminosilanes may be represented by the general formula:

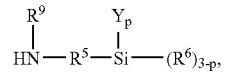

(XI)

wherein $R^9$ is H, $C_1$-$C_4$ alkyl, or $-R^5-Si(Y_p)(R^6)_{3-p}$;

$R^5$ is a divalent alkylene group, said alkylene groups optionally containing one or more catenary oxygen atoms;

Y is a hydrolysable group, $R^6$ is a monovalent alkyl or aryl group, p is 1, 2 or 3, preferably 3.

Some aminosilanes useful in the practice of this invention are described in U.S. Pat. No. 4,378,250 (Treadway et al., incorporated herein by reference) and include aminoethyltriethoxysilane, β-aminoethyltrimethoxysilane, β-aminoethyltriethoxysilane, β-aminoethyltributoxysilane, β-aminoethyltripropoxysilane, α-amino-ethyltrimethoxysilane, α-aminoethyltriethoxysilane, γ-aminopropyltrimethoxysilane, γ-aminopropyltrimethoxysilane, γ-aminopropyltriethoxysilane, γ-aminopropyltributoxysilane, γ-aminopropyltripropoxysilane, β-aminopropyltrimethoxysilane, β-aminopropyltriethoxysilane, β-aminopropyltripropoxysilane, β-aminopropyltributoxysilane, α-aminopropyltrimethoxysilane, α-aminopropyltriethoxysilane, α-aminopropyltributoxysilane, and α-aminopropyltripropoxysilane.

Minor amounts (<20 mole percent, relative to the total amount of amino silane) of catenary nitrogen-containing aminosilanes may also be used, including those described in U.S. Pat. No. 4,378,250 (Treadway et al., incorporated herein by reference. N-(β-aminoethyl)-β-aminoethyltrimethoxysilane, N-(β-aminoethyl)-β-aminoethyltriethoxysilane, N-(β-aminoethyl)-β-aminoethyltripropoxysilane, N-(β-aminoethyl)-α-aminoethyltrimethoxysilane, N-(β-aminoethyl)-α-aminoethyltriethoxysilane, N-(β-aminoethyl)-α-aminoethyltripropoxysilane, N-(β-aminoethyl)-β-aminopropyltrimethoxysilane, N-(β-aminoethyl)-γ-aminopropyltriethoxysilane, N-(β-aminoethyl)-γ-aminopropyltripropoxysilane, N-(β-aminoethyl)-γ-aminopropyltrimethoxysilane, N-(β-aminoethyl)-β-aminopropyltriethoxysilane, N-(β-aminoethyl)-β-aminopropyltripropoxysilane, N-(γ-aminopropyl)-β-aminoethyltrimethoxysilane, N-(γ-aminopropyl)-β-aminoethyltriethoxysilane, N-(γ-aminopropyl)-β-aminoethyltripropoxysilane, N-methylaminopropyltrimethoxysilane, β-aminopropylmethyl diethoxysilane, and γ-diethylene triaminepropyltriethoxysilane.

The coating compositions of this invention may contain silsesquioxanes. Useful silsesquioxanes include co-condensates of diorganooxysilanes (or hydrosylates thereof) of the formula $R^{10}{}_2Si(OR^{11})_2$ with organosilanes (or hydrosylates thereof) of the formula $R^{10}SiO_{3/2}$ where each $R^{10}$ is an alkyl group of 1 to 6 carbon atoms or an aryl group and $R^{11}$ represents an alkyl radical with 1 to 4 carbon atoms. Preferred silsesquioxanes are neutral or anionic silsesquioxanes, prior to addition to the composition. Useful silsesquioxanes can be made by the techniques described in U.S. Pat. No. 3,493,424 (Mohrlok et al.), U.S. Pat. No. 4,351,736 (Steinberger et al.), U.S. Pat. No. 5,073,442 (Knowlton et al.) U.S. Pat. No. 4,781,844 (Kortmann, et al), and U.S. Pat. No. 4,781,844, each incorporated herein by reference. A coating solution preferably comprises at least 90 wt. %, preferably at least 95 wt. %, and more preferably at least 99.5 wt. % silsesquioxane, relative to total solids (i.e. fluorochemical urethane of Formula I and silsesquioxane).

The silsesquioxanes may be prepared by adding silanes to a mixture of water, a buffer, a surface active agent and optionally an organic solvent, while agitating the mixture under acidic or basic conditions. It is preferable to add the quantity of silane uniformly and slowly in order to achieve a narrow particle size of 200 to 500 Angstroms. The exact amount of silane that can be added depends on the substituent R and whether an anionic or cationic surface-active agent is used. Co-condensates of the silsesquioxanes in which the units can be present in block or random distribution are formed by the simultaneous hydrolysis of the silanes. The amount of tetraorganosilanes, including tetralkoxysilanes and hydrosylates thereof (e.g. of the formula $Si(OH)_4$) present is less than 10 wt. %, preferably less than 5 wt. %, more preferably less than 2 wt. % relative to the weight of the silsesquioxane.

The following silanes are useful in preparing the silsesquioxanes of the present invention: methyltrimethoxysilane, methyltriethoxysilane, methyltriisopropoxyoxysilane, ethyltrimethoxysilane, ethyltriethoxysilane, propyltrimethoxysilane, isobutyltrimethoxysilane, isobutyltriethoxysilane, 2-ethylbutyltriethoxysilane, and 2-ethylbutoxytriethoxysilane.

The composition may be applied to the substrate by conventional techniques such as, for example, spraying, knife coating, notch coating, reverse roll coating, gravure coating, dip coating, bar coating, flood coating, or spin coating. Typically, the polymerizable composition is applied to the substrate as a relatively thin layer resulting in a dried cured layer having a thickness in a range of from about 40 nm to about 60 nm, although thinner and thicker (e.g., having a thickness up to 100 micrometers or more) layers may also be used. Next, any optional solvent is typically at least partially removed (e.g., using a forced air oven), and the composition is then at least partially cured to form a durable coating.

A preferred coating method for application of a fluorinated isocyanate silane of the present invention includes spray application. A substrate to be coated can typically be contacted with the treating composition at room temperature (typically, about 20 to about 25° C.). Alternatively, the mixture can be applied to substrates that are preheated at a temperature of for example between 60 and 150° C. This is of particular interest for industrial production, where e.g. ceramic tiles can be treated immediately after the baking oven at the end of the production line. Following application, the treated substrate can be dried and cured at ambient or elevated temperature, e.g. at 40 to 300° C. and for a time sufficient to dry. The process may also require a polishing step to remove excess material.

The present invention provides a protective coating on substrate that is relatively durable, and more resistant to contamination and easier to clean than the substrate surface itself. The present invention provides in one embodiment a method and composition for use in preparing a coated article comprising a substrate, preferably a hard substrate, and an antisoiling coating of greater than a monolayer (which is typically greater than about 15 Angstroms thick deposited thereon. Preferably an antisoiling coating of the present invention is at least about 20 Angstroms thick, and more preferably, at least about 30 Angstroms thick. Generally, the thickness of the coating is less than 10 micrometers, preferably less than 5 micrometers. The coating material is typically present in an amount that does not substantially change the appearance and optical characteristics of the article.

The coatings derived from the compounds of Formula I are particularly suitable for providing hydrophilic, oleophobic coatings. Such coatings cause water or moisture to wet out, while repelling oily contaminants. As result, the coatings provide a self-cleaning surface where contaminants may be removed under flowing water, and often without scrubbing. Such coatings are ideal for automotive, marine and household applications in which substrates such as glass, painted and clear coated surfaces, and rigid or flexible clear polymeric sheets may be rendered both hydrophilic and oleophobic. Such applications may include automobile body panels, windshields, boat hull and deck surfaces, flexible and rigid polymeric auto and marine windows, porcelain and ceramic surfaces, and countertops.

EXAMPLES

Materials

Desmodur™ N100, an aliphatic polyisocyanate resin based on hexamethylene diisocyanate (HDI) biuret, obtained from Bayer Polymers LLC of Pittsburgh, Pa.

Desmodur™ N3300A, an aliphatic polyisocyanate resin based on hexamethylene diisocyanate HDI trimer, obtained from Bayer Polymers LLC of Pittsburgh, Pa.

Materials

Methylisobutylketone (MIBK) was obtained from Burdick & Jackson Solvents, a unit of Honeywell International, Inc. Morris Township, N.J.

1,4-diazabicyclo[2.2.2]octane, DABCO™ 33LV, available from Air Product and Chemicals, Inc., Allentown, Pa.

Vazo™ 67 (2,2'-azobis(2-methylbutyronitrile)) was obtained from EI DuPont de Nemours & Co., Wilmington, Del.

(HFPOAmidol) was prepared by a procedure similar to that described in U.S. Pat. No. 7,094,829, entitled "Fluorochemical Composition Comprising a Fluorinated Polymer and Treatment of a Fibrous Substrate Therewith".

Aminopropyltriethoxy silane, (APTES) was obtained from Sigma-Aldrich 2-aminoethyl-3-aminopropyltrimethoxysilane (AEAPTMS) was obtained from Alfa-Aeser, Ward Hill, Mass.

Aminopropyltrimethoxy silane, (APTMS) was obtained from Sigma-Aldrich, Milwaukee, Wis.

N-methyl Aminopropyltrimethoxy silane (MAPTMS) was obtained from Union Carbide Chemicals and Plastics Co. of Danbury, Conn.

Bis(propyl-3-trimethoxysilane) amine was obtained from Gelest, Morrisville, Pa.

Mercaptopropyltrimethoxysilane was obtained from Sigma-Aldrich, Milwaukee, Wis.

Mercaptopropionic acid (MPA) was obtained from Sigma-Aldrich, Milwaukee, Wis.

Pentaerythritol triallyl ether (PEYA) was obtained from Sigma-Aldrich, Milwaukee, Wis. as a 70% technical grade solution.

Dibutyltin dilaurate (DBTDL) was obtained from Sigma-Aldrich, Milwaukee, Wis.

Dabco 33LV (triethylene diamine at 33% solids in dipropylene glycol) from Air Products and Chemicals

Example 1

Part a

To a 1 L flask was charged 20 g (0.102 eq NCO) Desmodur™ N3300A, 27.4 g (0.02 mol) HFPO amidol, 29.9 g solution (20.9 g solids, 0.082 mol) pentaerythritol allyl ether, and 250 g MIBK. The mixture was stirred and heated to 80° C. and a solution formed. The solution was purged with $N_2$ for 1 min and three drops each of dibutyltin dilaurate and DABCO™ 33LV was added. The resulting solution was heated to 110° C. for 18 H, after which the IR showed no NCO groups remaining. The solution was allowed to cool to 70° C. and 24 g (0.12 mol) mercaptopropyltrimethoxysilane and 9.5 g (0.12 mol) mercaptoethanol was added. The resulting solution was purged with $N_2$ for 3 minutes, 0.5 g Vazo™ 67 was added, and the resulting solution was heated for 16 hours, after which the IR showed no allylic groups remaining. The Fluorochemcial Urethane Silane Polyol was a solution at 27.1% solids.

Example 1

Part b—Aqueous Inversion

To a stirred and sonicated solution of 27.1 g solids (100 g solution) of the product of Example 1, part a, was added a solution of 1.8 g DS-10™ and 230 g deionized water at 80° C. The resulting emulsion was stirred and sonicated for 4 min, after which a stable emulsion of 15.5% solids resulted.

Example 2

Part a

To a 1 L flask was charged 20 g (0.102 eq NCO) Desmodur™ N3300A, 27.4 g (0.02 mol) HFPO amidol, 29.9 g solution (20.9 g solids, 0.082 mol) pentaerythritol allyl ether, and 250 g MIBK. The mixture was stirred and heated to 80° C. and a solution formed. The solution was purged with $N_2$ for 1 min and three drops each of dibutyltin dilaurate and DABCO™ 33LV was added. The resulting solution was heated to 110° C. for 18 hours, after which the IR showed no NCO groups remaining. The solution was allowed to cool to 70° C. and the 24 g (0.12 mol) mercaptopropyltrimethoxysilane and 18.4 g (0.12 mol) triethanolamine was added, followed by 13 g (0.12 mol) 3-mercaptopropionic acid. The resulting solution was cloudy and became clear after stirring for 5 min. The solution was purged with $N_2$ for 3 min and 0.5 g Vazo™ 67 was added. The resulting solution was heated for 16 H, after which the IR showed no allylic groups remaining. The product was a solution at 23.3% solids.

Example 2

Part b—Aqueous Inversion

To a stirring and sonicated solution of 23.3 g solids (100 g solution) of the products of Example 2, part a, was added a solution of 1.8 g DS-10™ and 230 g deionized water at 80° C. The resulting emulsion was stirred and sonicated for 4 minutes, resulting in a stable emulsion of 9.8% solids.

Examples 3-10

In each of the following examples, fluorochemical urethanes and emulsions thereof were prepared by the following procedure, using the reactants and amounts listed in Table 1.

To a 1 L flask was charged Desmodur™ N3300A, HFPO amidol, pentaerythritol allyl ether, and MIBK. The mixture was stirred and heated to 80° C. and a solution formed. The solution was purged with $N_2$ for 1 min and three drops each of dibutyltin dilaurate and DABCO™ 33LV was added. The resulting solution was heated to 110° C. for 18 hours, after which the IR showed no NCO groups remaining. The solution was allowed to cool to 70° C. and mercaptopropyltrimethoxysilane, triethanolamine was added, followed by 3-mercaptopropionic acid was added. The resulting solution was cloudy and became clear after stirring for 5 minutes. The solution was purged with $N_2$ for 3 minutes and 1 wt. % (based on total solids) Vazo™ 67 was added. The resulting solution was heated for 16 after which the IR showed no allylic groups remaining.

The fluorochemical urethane silane was added to a stirred and sonicated solution of 7% (based on total solids) DS-10 and dionized water (sufficient to make a 10% solids emulsion after solvent removal) at 80° C. The resulting emulsion was stirred and sonicated for 4 minutes resulting in a stable emulsion.

TABLE 1

| Example | N3300 (g) | HFPO-amidol (g) | pentaerythritol allyl ether (g) | MPTMS (g) | MPA (g) | HOEt₃N 9 g) | MIBK (g) |
|---|---|---|---|---|---|---|---|
| 3 | 15 | 5.1 | 18.79 | 8.6 | 17.4 | 12.2 | 200 |
| 4 | 15 g | 8.6 g | 18.1 g | 27.8 | 5.6 | 7.9 | 186 |
| 5 | 15 | 34.5, | 13.19 | 12.6 | 4.0 g | 5.6 | 270 |
| 6 | 15 g | 19.9 | 15.98 gs | 7.3 | 12.1 | 17 | 200 |
| 7 | 15 | 0.0% | 19.78 gs | 27.7 g | 13.3 | 18.6 | 212 |
| 8 | 15 | 34.5 | 13.19 | 9.3 g | 5.8 | 8.2 | 315 |
| 9 | 15 | 21.5 | 15.6 | 19.4 | 4.8 | 6.8 | 221 |
| 10 | 15 | 13.78 | 17.1 | 15.7 | 9.9 | 13.9 | 192 |

Examples 11-18

In each of the following examples, fluorochemical urethanes and emulsions thereof were prepared by the following procedure, using the reactants and amounts listed in Table 2.

Preparation of Monoallyltrimethoxysilane Alcohol (MATS-OH)

To a flask was added 170 g (0.89 mol) mercaptopropyltrimethoxysilane, 50 g (0.89 mol) allyl alcohol, 1 g V-67, and 300 g MIBK. The solution was stirred and purged with $N_2$ for 4 minutes. The solution was heated to 60° C. for 18 hours. The final solution was 40% solids.

To a 1 L flask was charged Desmodur™ N3300A, HFPO amidol, pentaerythritol allyl ether, monoallyltrimethoxysilane alcohol (supra) and MIBK. The mixture was stirred and heated to 80° C. and a solution formed. The solution was purged with $N_2$ for 1 min and three drops each of dibutyltin dilaurate and DABCO™ 33LV was added. The resulting solution was heated to 110° C. for 18 hours, after which the IR showed no NCO groups remaining. The solution was allowed to cool to 70° C. and mercaptopropyltrimethoxysilane and triethanolamine was added, followed by 3-mercaptopropionic acid. The resulting solution was cloudy and became clear after stirring for 5 minutes. The solution was purged with $N_2$ for 3 minutes and 1% wt (based on total solids) Vazo™ 67 was added. The resulting solution was heated for 16 hours, after which the IR showed no allylic groups remaining.

The fluorochemical urethane silane was added to a stirred and sonicated solution of 7% (based on total solids) DS-10 and dionized water (sufficient to make a 10% solids emulsion after solvent removal) at 80° C. The resulting emulsion was stirred and sonicated for 4 minutes resulting in a stable emulsion. Comparative example C-1 was prepared as in the other example with no fluorochemical.

Laboratories, Hillsdale, Mich.) were painted metal panels with a urethane acrylate clearcoat (RK8014, available from DuPont) typical for a car. The test panels were coated, cured for 30 minutes at room temperature, and aged for 24 hours at a room temperature in a desiccation box.

The abrasion testing was essentially as described in ASTM D 2486-00, "Scrub Resistance of Wall Paints" using a BYK Gardener Abrasion Tester operating at 37 cycles/min. and equipped with a weighted sponge assembly of 150 gm weight, with an O-Cello™ sponge and an abrasion surface area of 4"×3". The test is run with the coated sample submerged in deionized water; and the sponge is saturated beforehand with deionized water.

The test is run for 100 cycles. Surface abrasion/wear is evaluated then by visual inspection against a standard. The visual ranking scale is as follows:

1=All coating removed

2=Less than 50% of coating (by surface area) remains

3=Greater than 50% but less than 100% of coating remains

4=Coating is intact over all the surface but exhibits scratches

5=Coating is intact and pristine (no visible scratching)

Haze/Gloss Testing

A 5% solids coating solution of 95:5 wt. % fluorochemical urethane:APTES (3-aminopropyltriethoxysilane) in 9:1 isopropanol/water was prepared. The clearcoated test panels were coated with the coating solution, then drained and dried

TABLE 2

| Example | N3300 (g) | HFPO amidol (g) | MATS-OH (g) | PETA (g) | MPA (g) | HOET$_3$N (g) | MIBK (g) |
|---|---|---|---|---|---|---|---|
| 11 | 15 | 5.1 | 3.9 | 14.8 | 18.3 | 11.6 | 168 |
| 12 | 15 | 8.6 | 13.1 | 5 | 6 | 8.5 | 149 |
| 13 | 15 | 34.5 | 13.8 | 5 | 6 | 8.5 | 187 |
| 14 | 15 | 19.9 | 3.9 | 12 | 14.8 | 10.4 | 167 |
| C-1 | 15 | 0.0% | 8.9 | 10.7 | 13.2 | 9.2 | 150 |
| 15 | 15 | 34.5 g, | 6 | 7 | 8.7 | 7.3 | 150 |
| 16 | 15 | 21.5 | 10.6 | 5 | 6 | 8.5 | 145 |
| 17 | 15 | 13.78 | 7.8 | 9.2 | 11.4 | 8 | 143 |

Abrasion Testing

A coating solution of the fluorochemical urethane of the indicated Example and an aminosilane was prepared at 5 wt. % solids using a 90:10 mixture of water and isopropanol as solvent, and also containing 3.5 wt. % N-methyl pyrrolidone. The aminosilanes tested were 3-aminopropyltriethoxysilane (APTES), 3-aminopropyltrimethoxysilane (APTMS) and 2-aminoethyl-3-aminopropyltrimethoxysilane (AE-APTMS).

The coating solution was aged for 16 hours at room temperature. The test panels, (available as APR 4861F, from ACT while maintaining the test panels at a 70° angle, then aged for about 24 hours in a dessication box at ambient temperature. The coated panels were then rinsed with tap water, and dried under a nitrogen stream. In examples 12 and 13, a 5.4% solids solution was prepared with no aminosilane, which was coated and tested as the other examples.

Haze and gloss were measured using a BYK Gardner Haze-Gloss Reflectometer model 4601. Three readings were taken and the average recorded. Gloss was measured at at both 20° and 60°, and haze was measured at 20°. The results are shown in Table 3.

TABLE 3

| Notebook/Example | Urethane Example No. | Abrasion Rating | pre abrasion Haze | post abrasion Haze | delta | pre abrasion 20 Gloss | post abrasion 20 Gloss | delta | pre abrasion 60 Gloss | post abrasion 60 Gloss | delta |
|---|---|---|---|---|---|---|---|---|---|---|---|
| 18 | 3 | 3 | 46 | 16 | −30 | 62 | 84 | 23 | 75 | 92 | 17 |
| 19 | 4 | 5 | 15 | 18 | 3 | 67 | 70 | 3 | 83 | 85 | 2 |
| 20 | 5 | 5 | 20 | 13 | −7 | 40 | 75 | 35 | 66 | 86 | 20 |
| 21 | 6 | 4 | 11 | 6 | −5 | 54 | 86 | 32 | 71 | 93 | 22 |

TABLE 3-continued

| Notebook/ Example | Urethane Example No. | Abrasion Rating | pre abrasion Haze | post abrasion Haze | delta | pre abrasion 20 Gloss | post abrasion 20 Gloss | delta | pre abrasion 60 Gloss | post abrasion 60 Gloss | delta |
|---|---|---|---|---|---|---|---|---|---|---|---|
| 22 | 7 | 5 | 24 | 10 | −15 | 83 | 88 | 5 | 92 | 94 | 2 |
| 23 | 7 | 4 | 115 | 116 | 1 | 35 | 41 | 6 | 58 | 64 | 6 |
| 24 | 8 | 5 | 35 | 26 | −10 | 10 | 60 | 49 | 31 | 74 | 43 |
| 25 | 9 | 4 | 5 | 6 | 1 | 23 | 89 | 65 | 7 | 94 | 87 |
| 26 | 10 | 4 | 25 | 40 | 16 | 81 | 57 | −23 | 90 | 86 | −4 |
| 27 | 11 | 2 | 14 | 15 | 1 | 64 | 62 | −2 | 82 | 81 | 0 |
| 28 | 12 | 4 | 47 | 50 | 4 | 65 | 63 | −2 | 81 | 80 | −1 |
| 29 | 13 | 2 | 13 | 15 | 2 | 74 | 67 | −7 | 86 | 83 | −3 |
| 30 | 14 | 1 | 74 | 91 | 17 | 60 | 50 | −10 | 82 | 77 | −5 |
| C2 | C-1 | 1 | 9 | 8 | −1 | 89 | 80 | −10 | 96 | 93 | −4 |
| 31 | 15 | 3 | 116 | 117 | 1 | 54 | 55 | 1 | 72 | 73 | 1 |
| 32 | 16 | 2 | 34 | 37 | 4 | 66 | 66 | 0 | 83 | 82 | −1 |
| 33 | 17 | 1 | 16 | 16 | 0 | 71 | 70 | −1 | 86 | 85 | −2 |
| 34 | 2b | 3 | 21 | 19 | −2 | 66 | 72 | 6 | 82 | 83 | 1 |
| Untreated Control Panel C3 | — | | 9.4 | 6 | −3 | 87 | 88 | 2 | 93 | 94 | 1 |

Method for Measuring Contact Angles

The painted metal test panels (prepared as described above) were rinsed for 30 seconds with water to remove any surface surfactants. Measurements were made using as-received reagent-grade hexadecane and de-ionized water filtered through a filtration system (obtained from Millipore Corporation Billerica, Mass.), on a video contact angle analyzer (available as product number VCA-2500XE from AST Products Billerica, Mass.). Reported values are the averages of measurements on at least three drops measured on the right and the left sides of the drops. Drop volumes were 5 μL for static measurements. The results are shown in Table 4.

For comparative purposes, an uncoated panel (from comparative example 1), and panels coated with 3M Performance Finish (a commercial synthetic wax available from the 3M Company) and "A Touch of Class, Special Edition Paint Protector Renewer (available from CAL-TEX Protective Coatings, Inc., Schertz, Tex.) are provided.

TABLE 4

| Panel | Hexadecane Static (Avg) | Hexadecane Receding (Avg) | Water Static (Avg) | Water Receding (Avg) |
|---|---|---|---|---|
| 18 | 51 | 34 | 78 | |
| 19 | 60 | 26 | 102 | |
| 20 | 72 | 39 | 107 | |
| 21 | 62 | 40 | 102 | 46 |
| 22 | 12 | 23 | 44 | 44 |
| 23 | 5 | 25 | 53 | 44 |
| 24 | 59 | 37 | 97 | 54 |
| 25 | 63 | 23 | 81 | 50 |
| 26 | 56 | 31 | 80 | 45 |
| 27 | 58 | 14 | 85 | 61 |
| 28 | 26 | 22 | 76 | 63 |
| 29 | 83 | 27 | 115 | 65 |
| 30 | 57 | 26 | 76 | 60 |
| C-2 | 14 | 29 | 77 | 60 |
| 31 | 66 | 49 | 104 | 53 |
| 32 | 66 | 33 | 105 | 56 |
| 33 | 61 | 26 | 75 | 56 |
| 34 | 70 | | 74 | |
| Perform. Finish C4 | 26 | | 99 | |
| Touch of Class C5 | <5 | | 89 | |
| Blank Control C3 | <5 | | 85 | |

The invention claimed is:

1. A compound of the formula

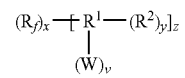

wherein $R_f$ is

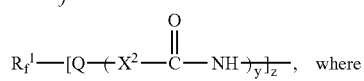

$R_f^1$ is a monovalent perfluoroalkyl or a perfluorooxyalkyl group, or a divalent perfluoroalkylene or a perfluorooxyalkylene group, Q is a covalent bond, or a polyvalent alkylene group of valency z, X is —O—, —NR$^4$— or S—, where R$^4$ is H or C$_1$-C$_4$ alkyl, y is 1 or 2, and z is independently 1 or 2, R$^1$ is the residue of a polyisocyanate selected from multivalent aliphatic, alicyclic, or aromatic moiety, W is

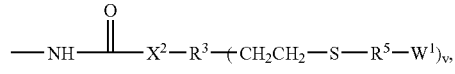

where W$^1$ is a water-solubilizing group selected from carboxylate, sulfate, sulfonate, phosphate, phosphonate, ammonium, quaternary ammonium, poly(oxyalkylene), and mixtures thereof, X$^4$ is —O—, —NR$^4$— or —S—, where R$^4$ is H or C$_1$-C$_4$ alkyl;

and v is 1 or 2;

R$^2$ is of the formula:

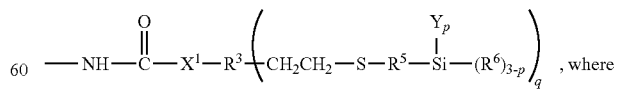

where

Y is a hydrolysable group selected from a halide, a C$_1$-C$_4$ alkoxy group, an acyloxy group or a polyoxyalkylene group, R$^6$ is a monovalent alkyl or aryl group, p is 1, 2 or 3, and q is 1 to 5;

each $R^5$ is a divalent alkylene group, said alkylene groups optionally containing one or more catenary oxygen atoms;

each $X^1$ is —O— or —NR$^4$—, where R$^4$ is H or $C_1$-$C_4$ alkyl, each $R^3$ is a polyvalent alkylene or arylene groups, or combinations thereof, said alkylene groups optionally containing one or more catenary oxygen atoms;

x and y are each independently at least 1, and z is independently 1 or 2.

2. The compounds of claim 1 wherein $R_f^1$ comprises a perfluorooxyalkylene group comprising perfluorinated repeating units selected from the group consisting of —($C_nF_{2n}$O)—, —(CF(Z)O)—, —(CF(Z)$C_nF_{2n}$O)—, —($C_nF_{2n}$CF(Z)O)—, —($CF_2$CF(Z)O)—, and combinations thereof, wherein n is 1 to 4 and Z is a perfluoroalkyl group, a perfluoroalkoxy group, or perfluoroether group.

3. The compounds of 1 wherein $R_f^1$ comprises a group of the formula $R_f^6$—$R_f^3$—O—O—$R_f^4$—$(R_f^5)_q$.

wherein $R_f^6$ is F for monovalent perfluorooxyalkyl, and an open valence ("–") for divalent perfluorooxyalkylene;

$R_f^3$ represents a perfluoroalkylene group, $R_f^4$ represents a perfluoroalkyleneoxy group consisting of periluoroalkyleneoxy groups having 1, 2, 3 or 4 carbon atoms or a mixture of such periluoroalkyleneoxy groups, $R_f^5$ represents a perfluoroalkylene group, and q is 0 or 1.

4. The compound of claim 1 wherein said periluorooxyalkylene group is selected from one or more of [$CF_2CF_2O$]$_r$; —[CF($CF_3$)—$CF_2$—O]$_s$—; [$CF_2CF_2O$]$_r$—[$CF_2O$]$_t$, —[$CF_2CF_2CF_2CF_2$—O]$_u$ and [$CF_2CF_2O$]$_r$,[CF($CF_3$)$CF_2O$]$_s$; wherein each of r, s, t and u each are integers of 1 to 50.

5. The compounds of claim 1 wherein $R_f$ is a monovalent perfluorooxyalikylene group and z is 1.

6. The compounds of claim 1 wherein the molar ratio of silane groups to —NH—C(O)—$X^1$— groups is greater than 1:1.

7. The compounds of claim 1 wherein $R_f$ is derived from a fluorinated polyol.

8. The compounds of claim 1, derived from the free-radical addition of a thiosilane to an ethylenically unsaturated group.

9. The compounds of claim 1, wherein Y is a halogen, a $C_1$-$C_4$ alkoxy group, or a $C_1$-$C_4$ acyloxy group.

10. The compounds of claim 1 wherein the water solubilizing group $W^1$ is represented by —$CO_2$M, —OH, —$OSO_3$M, —$SO_3$M, —PO(OM)$_2$, —P(OM)$_3$, and —N($R^8$)$_3$ X, wherein each $R^8$ is selected from the group consisting of a phenyl group, a cycloaliphatic group, or an aliphatic group having from about 1 to 12 carbon atoms, M is H or one equivalent of a monovalent or divalent soluble cation selected from sodium, potassium, calcium, and N($R^4$)$_3$H+, $R^4$ is H or $C_1$-$C_4$ alkyl, and X is a soluble anion.

11. A coating composition comprising at least one compound of claim 1 and a solvent.

12. The composition of claim 11 further comprising an aminosilane.

13. A coating composition comprising an aqueous dispersion or suspension of the compounds of claim 1.

14. The coating composition of claim 11, further comprising an silsequioxane.

15. A compound of claim 1 comprising the free radical reaction product of a thiosilane with a fluorochemical urethane compound having pendent ethylenically unsaturated groups, said fluorochemical urethane compound comprising the reaction product of a polyisocyanate, a nucleophilic fluorinated compound, a nucleophilic water-solubilizing compound and a nucleophilic ethylenically unsaturated compound.

16. A method of preparing the compound of claim 1 comprising the step of free radical addition of a thiosilane to a urethane compound of the formula:

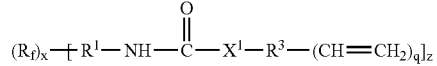

wherein $R_f$ is a perfluorinated group, $R^1$ is the residue of a polyisocyanate, $X^1$ is —O— or —NR$^4$—, where R$^4$ is H or $C_1$-$C_4$ alkyl, $R^3$ is a divalent alkylene or arylene groups, or combinations thereof, said alkylene groups optionally containing one or more catenary oxygen atoms;

z is independently 1 or 2, x is 1 or 2; and q is 1 to 5.

17. The method of claim 16 wherein the thiosilane is of the formula

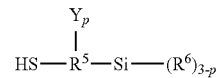

wherein $R^5$ is a divalent alkylene group, said alkylene groups optionally containing one or more catenary oxygen atoms;

Y is a hydrolysable group, $R^6$ is a monovalent alkyl or aryl group, and p is 1, 2 or 3.

18. The method of claims 16 wherein the moiety —$R^3$—(CH=$CH_2$) comprises a vinyl group, an allyl group or an allyloxy group.

19. A method of preparing the compound of claim 1 comprising the step of free radical addition of a water-solubilizing compound of the formula HS—$R^5$—$W^1$, wherein $R^5$ is a divalent alkylene group, said alkylene groups optionally containing one or more catenary oxygen atoms, and $W^1$ is a water-solubilizing group;

to a urethane compound of the formula:

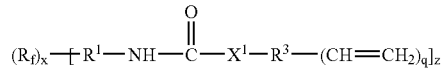

wherein $R_f$ is a perfluorinated group, $R^f$ is the residue of a polyisocyanate, $X^1$ is —O— or —NR$^4$—, where R$^4$ is H or $C_1$-$C_4$ alkyl, $R^3$ is a divalent alkylene or arylene groups, or combinations thereof, said alkylene groups optionally containing one or more catenary oxygen atoms;

z is independently 1 or 2, and q is 1 to 5.

20. A method of preparing the compound of claim 1 comprising the step of free radical addition of a water-solubilizing compound of the formula HS—$R^5$—$W^1$, wherein $R^5$ is a divalent alkylene group, said alkylene groups optionally containing one or more catenary oxygen atoms, and $W^1$ is a water-solubilizing group; and free-radical addition of a thiosilane, to a urethane compound of the formula:

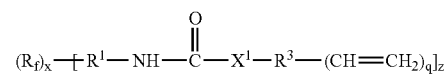
wherein
$R_f$ is a perfluorinated group,
$R^1$ is the residue of a polyisocyanate,
$X^1$ is —O— or —$NR^4$—, where $R^4$ is H or $C_1$-$C_4$ alkyl,
$R^3$ is a divalent alkylene or arylene groups, or combinations thereof, said alkylene groups optionally containing one or more catenary oxygen atoms;
z is independently 1 or 2, and
q is 1 to 5.
* * * * *

UNITED STATES PATENT AND TRADEMARK OFFICE
CERTIFICATE OF CORRECTION

PATENT NO. : 7,652,116 B2  Page 1 of 1
APPLICATION NO. : 11/765914
DATED : January 26, 2010
INVENTOR(S) : Gregory D Clark It is certified that error appears in the above-identified patent and that said Letters Patent is hereby corrected as shown below:

Title Page, Column 2,
Item (74), please delete "Kent S. Kokks" and insert -- Kent S. Kokko --.

Signed and Sealed this

Third Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,652,116 B2
APPLICATION NO. : 11/765914
DATED : January 26, 2010
INVENTOR(S) : Gregory D Clark It is certified that error appears in the above-identified patent and that said Letters Patent is hereby corrected as shown below:

Column 2,
Line 28, delete "acylic," and insert -- acyclic, --.

Column 3,
Line 29, after "like" insert -- . --.

Column 4,
Line 49, below "2 to 5," insert -- x and y are each independently at least 1, and z is independently 1 or 2. --.

Column 7,
Line 25, delete " $R_f^6 \cdot R_f^3 - O - R_f^4 - (R_f^5)_q -$ " and insert -- $R_f^6 - R_f^3 - O - R_f^4 - (R_f^5)_q -$ --.

Column 12,
Lines 59-60 delete " $\sim R^3 - CH = CH_2 + HS - R^5 \sim \rightarrow \sim R^3 - CH_2 - CH_2 - S - R^5$ and/or $R^3 - CH(CH_3) - S - R^5 \sim$ " and insert -- $\sim R^3 - CH = CH_2 + HS - R^5 \sim \rightarrow \sim R^3 - CH_2 - CH_2 - S - R^5 \sim$ and/or $\sim R^3 - CH(CH_3) - S - R^5 \sim$ --.

Column 15,
Line 46, delete " $R_f^2[-(L)_a - Z]_b$ " and insert -- $R_f^2[-(L)_a - Z]_b$ --.

Signed and Sealed this

Tenth Day of August, 2010

David J. Kappos
*Director of the United States Patent and Trademark Office*

CERTIFICATE OF CORRECTION (continued)

U.S. Pat. No. 7,652,116 B2

Column 17,
Line 24, delete "tetralkoxysilanes" and insert -- tetraalkoxysilanes --.

Column 22,
Line 53, after "measured at" delete "at".

Column 24,
Line 39, in claim 1, delete "X" and insert -- $X^2$ --.
Line 39, in claim 1, delete "S—," and insert -- —S— --.
Line 54, in claim 1, delete "$X^4$" and insert -- $X^2$ --.

Column 25,

Line 20, in claim 3, delete " $R_f^6—R_f^3—O—O—R_f^4—(R_f^5)_q.$ " and insert

-- $R_f^6\text{-}R_f^3\text{-}O\text{-}R_f^4\text{-}(R_f^5)_q\text{-}$ --.

Column 25,
Line 25, in claim 3, delete "periluoroalkyleneoxy" and
insert -- perfluoroalkyleneoxy --.

Column 25,
Line 27, in claim 3, delete "periluoroalkyleneoxy" and
insert -- perfluoroalkyleneoxy --.

Column 25,
Lines 30-31, in claim 4, delete "periluorooxyalkylene" and insert -- perfluorooxyalkylene --.

Column 25,
Line 31, in claim 4, delete "$[CF_2CF_2O]_r$," and insert -- $\text{-}[CF_2\text{-}O]_r\text{-}$ --.

Column 25,
Line 33, in claim 4, delete "$[CF_2CF_2O]_r$," and insert -- $\text{-}[CF_2\text{-}CF_2O]_r$ --.

Column 25,
Line 36, in claim 5, delete "perfluorooxyalikylene" and insert -- perfluorooxyalkylene --.

Line 62, in claim 14, delete "silsequioxane." and insert -- silsesquioxane. --.

Column 26,
Line 53, in Claim 19, delete "$R^f$" and insert -- $R^1$ --.